(12) United States Patent
Prevost et al.

(10) Patent No.: US 8,961,566 B2
(45) Date of Patent: Feb. 24, 2015

(54) VERTEBRAL CONSTRUCT AND METHODS OF USE

(75) Inventors: Julien J. Prevost, Memphis, TN (US); Hai H Trieu, Cordova, TN (US); Ian Rubin de la Borbolla, Memphis, TN (US)

(73) Assignee: Warsaw Othopedic, Inc., Warsaw, IN (US)

( * ) Notice: Subject to any disclaimer, the term of this patent is extended or adjusted under 35 U.S.C. 154(b) by 239 days.

(21) Appl. No.: 13/358,992

(22) Filed: Jan. 26, 2012

(65) Prior Publication Data

US 2013/0197582 A1    Aug. 1, 2013

(51) Int. Cl.
*A61B 17/88* (2006.01)

(52) U.S. Cl.
USPC ............................................. 606/254

(58) Field of Classification Search
USPC .................................. 606/250–278
See application file for complete search history.

(56) References Cited

U.S. PATENT DOCUMENTS

| | | | |
|---|---|---|---|
| 2005/0277922 A1* | 12/2005 | Trieu et al. | 606/61 |
| 2008/0262546 A1* | 10/2008 | Calvosa et al. | 606/250 |
| 2009/0275986 A1* | 11/2009 | Prevost et al. | 606/278 |
| 2009/0287252 A1* | 11/2009 | Marik et al. | 606/278 |

* cited by examiner

*Primary Examiner* — Mary Hoffman
*Assistant Examiner* — Tara R Carter

(57) ABSTRACT

A vertebral construct comprises a longitudinal element extending between a first end and a second end. The longitudinal element defines a central axis. A first spacer is mounted to the longitudinal element. A second spacer is mounted to the longitudinal element. A flexible element is disposed about the longitudinal element and between the first spacer and the second spacer. The flexible element defines a central axis offset from the central axis of the longitudinal element. Methods of use are disclosed.

20 Claims, 9 Drawing Sheets

VERTEBRAL CONSTRUCT AND METHODS OF USE

TECHNICAL FIELD

The present disclosure generally relates to medical devices for the treatment of spinal disorders, and more particularly to a dynamic vertebral construct, which may include flexion, extension and/or lateral motion capability to provide stability while reducing stress on spinal elements.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. During surgical treatment, one or more rods may be fastened to the exterior of two or more vertebral members to provide stability to a treated region. This disclosure describes an improvement over these prior art technologies.

SUMMARY

Accordingly, a vertebral construct is provided. In one embodiment, in accordance with the principles of the present disclosure, a vertebral construct comprises a longitudinal element extending between a first end and a second end. The longitudinal element defines a central axis. A first spacer is mounted to the longitudinal element. A second spacer is mounted to the longitudinal element. A flexible element is disposed about the longitudinal element and between the first spacer and the second spacer. The flexible element defines a central axis offset from the central axis of the longitudinal element.

In one embodiment, the vertebral construct comprises a longitudinal element extending between a first end and a second end, and defines a central axis. A first rigid spacer includes an inner surface that defines a cavity configured for disposal of the longitudinal element therein. A second rigid spacer includes an inner surface that defines a cavity configured for disposal of the longitudinal element therein. A resistance element includes an inner surface that defines a cavity configured for disposal about the longitudinal element. The resistance element is further disposed between the first spacer and the second spacer. The resistance element defines a central axis offset from the central axis of the longitudinal element.

In one embodiment, the vertebral construct comprises a tether extending between a first end and a second end, and defining a central axis. A first fixation element is mounted adjacent the first end of the tether. A first rigid spacer includes an inner surface that defines a cavity configured for disposal of the tether therein, The first rigid spacer is disposed adjacent the first fixation element. A second rigid spacer includes an inner surface that defines a cavity configured for disposal of the tether therein. A resistance element includes an inner surface that defines a cavity configured for disposal about tether. The resistance element is further disposed between the first spacer and the second spacer. The resistance element defines a central axis offset from the central axis of the tether. A second bone fastener is mounted to the tether and is disposed between the first spacer and the resistance element. A first rigid cap is disposed between the second bone fastener and the first spacer. A second rigid cap is disposed between the second bone fastener and the resistance element. A third bone fastener is mounted to the tether and is disposed between the second spacer and the resistance element. A third rigid cap is disposed between the third bone fastener and the resistance element. A fourth rigid cap is disposed between the third bone fastener and the second spacer.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
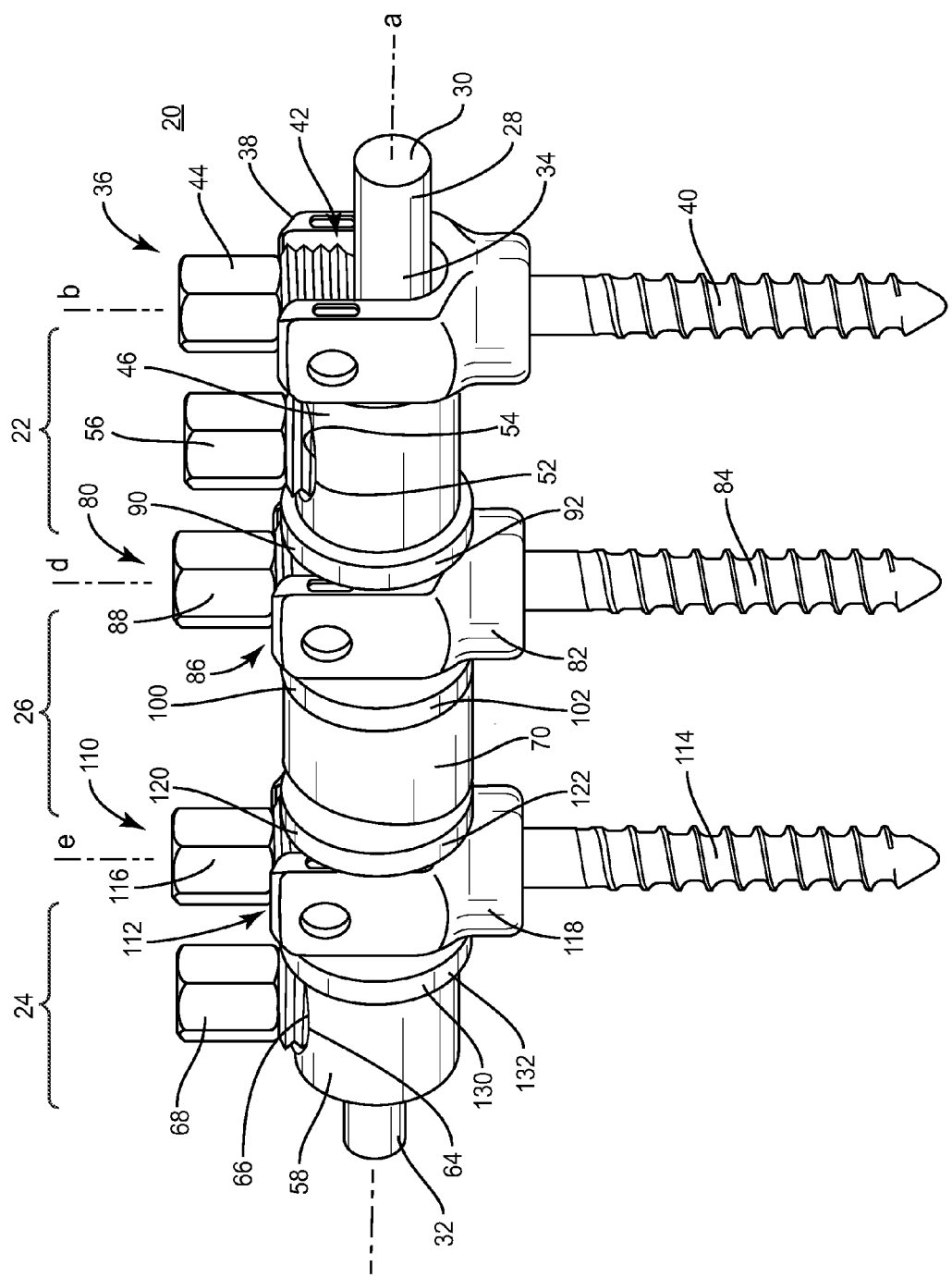
FIG. 1 is a perspective view of one embodiment of a vertebral construct in accordance with the principles of the present disclosure.

The exemplary embodiments of a surgical system and methods of use disclosed are discussed in terms of medical devices for the treatment of spinal disorders and more particularly, in terms of a dynamic vertebral construct, which may include flexion, extension and/or lateral motion capability to provide stability while reducing stress on spinal elements. It is envisioned that the vertebral construct can include a non-concentric intermediate portion for dynamic stabilization applications.

In one embodiment, the vertebral construct is employed as a posterior pedicle screw based dynamic stabilization system for the spine. In one embodiment, the vertebral construct includes at least one resistance member disposed between two rigid spacers. It is contemplated that the resistance member can be fabricated from elastic compressible materials, such as polyurethane or silicone. It is further contemplated that the rigid spacers are tied to pedicle screws by standard connectors, such as a set screw.

In one embodiment, the vertebral construct is attached by a longitudinal element such as a cable or a tether through at least one spacer. In one embodiment, the tether and/or cable is disposed in a non-concentric orientation with the resistance member(s) and/or spacer(s). In one embodiment, the tether and/or cable has an axis offset from the axis of the resistance member(s) and/or spacer(s). These configurations provide a selective and/or controlled damping to the vertebral construct. These configurations also provide disposal of the resistance member(s) and/or spacer(s) independent of the placement of the pedicle screws, and provide access to the vertebral construct.

It is envisioned that the cable or tether may be disposed adjacent to the at least one spacer and is tensioned by rigid caps on either side of the pedicle screws. It is further contemplated that this configuration of the vertebral construct provides stability in flexion-extension as well as lateral bending motion. The resistance member may have different sizes and shapes to provide a selected amount of distraction between vertebrae. It is envisioned that the tether and/or cable can be rigid or flexible depending on the level of selected flexion. In one embodiment, the vertebral construct can include a cap that can transition to a rigid rod to facilitate fusing adjacent vertebral levels.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
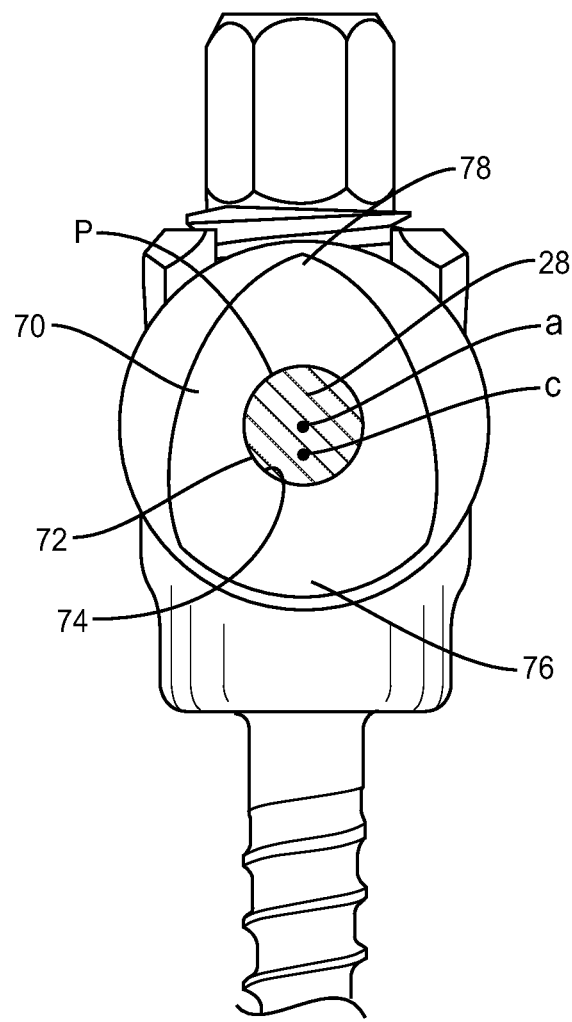
FIG. 2 is a plan view in part cross section of the vertebral construct shown in FIG. 1.

The following discussion includes a description of a surgical system including a vertebral construct, related components and exemplary methods of employing the vertebral construct in accordance with the principles of the present disclosure. Alternate embodiments are also disclosed. Reference will now be made in detail to the exemplary embodiments of the present disclosure, which are illustrated in the accompanying figures. Turning now to FIGS. 1 and 2, there is illustrated components of a surgical system including a vertebral construct 20 in accordance with the principles of the present disclosure.

The components of the surgical system can be fabricated from biologically acceptable materials suitable for medical applications, including metals, synthetic polymers, ceramics and bone material and/or their composites, depending on the particular application and/or preference of a medical practitioner. For example, the components of vertebral construct 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/ or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the surgical system may have material composites, including the above materials, to achieve various desired characteristics such as strength, rigidity, elasticity, compliance, biomechanical performance, durability and radiolucency or imaging preference. The components of the surgical system, individually or collectively, may also be fabricated from a heterogeneous material such as a combination of two or more of the above-described materials. The components of the surgical system may be monolithically formed, integrally connected or include fastening elements and/or instruments, as described herein.

For example, the various components of vertebral construct 20 can be formed of two or more materials. In one embodiment, a tether, spacers and/or caps can be fabricated from carbon-reinforced PEEK and a flexible element can be fabricated from PEEK. In one embodiment, a tether, spacers and/or caps are fabricated from PEEK and a flexible element is fabricated from carbon-reinforced. PEEK. In one embodiment, alternate materials may be employed in a radial direction of the tether such that stiff materials such as metals or other composites are used in a core of the tether and an outer sheet of lower modulus polymeric material is used in the outer radial portion of the tether, or vice versa. In one embodiment employing a composite material similar to those described, the tether can have a cylindrical geometry and the intermediate section can have a rectangular or oblong geometry.

As a further example, a flexible element or a resistance element of vertebral construct 20 may be fabricated from materials such as silicone, polyurethane, silicone-polyurethane copolymers, polymeric rubbers, polyolefin rubbers, hydrogels, semi-rigid and rigid materials, and biocompatible materials such as elastomers, rubbers, thermoplastic elastomers, thermoset elastomers, elastomeric composites and plastics. It is envisioned that the construct sections can be manufactured from, for example, machining and milling from a solid stock material and/or injection molding. The flexible element or resistance element can be manufactured from, for example, machining and milling, extrusion and die cutting, injection molding, transfer molding and/or cast molding.

Vertebral construct 20 is configured for attachment to vertebrae (as shown, for example, in FIG. 3) during surgical treatment of a spinal disorder, examples of which are discussed herein. It is contemplated that there may be variations of the number of elements disclosed for vertebral construct 20. As shown in FIGS. 1 and 2, vertebral construct 20 includes an upper section 22, an intermediate section 26 and a lower section 24.

Intermediate section 26 is connected with sections 22, 24 and disposed therebetween as a joining section of vertebral construct 20. It is envisioned that the components of vertebral construct 20 may be monolithically formed, integrally connected or arranged with attaching elements. Intermediate section 26 is flexible relative to sections 22, 24, and is configured to provide resistance to movement of sections 22, 24. It is envisioned that intermediate section 26 may provide increasing, variable, constant and/or decreasing resistance. It is contemplated that sections 22, 24, 26 can be variously dimensioned, for example, with regard to length, width, diameter and thickness. It is further contemplated that the respective cross-section of sections 22, 24, 26 may have various configurations, for example, round, oval, rectangular, irregular, uniform and non-uniform. Section 22 may have a different cross-sectional area, geometry, material or material property such as strength, modulus or flexibility relative to section 24.

Vertebral construct 20 includes a longitudinal element, such as, for example, a tether 28 extending between a first end 30 and a second end 32. Tether 28 defines a central axis a. Tether 28 includes an outer circumferential surface 34 that defines a perimeter P. It is envisioned that all or only a portion of tether 28 may have a semi-rigid, rigid or elastic configuration, and/or have elastic properties such that tether 28 provides a selective amount of expansion and/or extension in an axial direction. It is further envisioned that tether 28 may be compressible in an axial direction. Tether 28 can include a plurality of separately attachable or connectable portions or sections, such as bands or loops, or may be monolithically formed as a single continuous element.

Tether 28 has a uniform thickness/diameter. It is envisioned that tether 28 may have various surface configurations, such as, for example, rough, threaded for connection with surgical instruments, arcuate, undulating, porous, semi-porous, dimpled, polished and/or textured according to the requirements of a particular application. It is contemplated that the thickness defined by tether 28 may be uniformly increasing or decreasing, or have alternate diameter dimensions along its length. It is further contemplated that tether 28 may have various cross section configurations, such as, for example, oval, oblong, triangular, rectangular, square, polygonal, irregular, uniform, non-uniform, variable and/or tapered.

It is contemplated that tether 28 may have various lengths, according to the requirements of a particular application. It is further contemplated that tether 28 may be braided, such as a rope, or include a plurality elongated elements to provide a predetermined force resistance.

A first fixation element, such as, for example, a bone fastener 36 is mounted adjacent the first end 30. Bone fastener 36 is elongated along an axis b, which is oriented transverse to axis a. Bone fastener 36 comprises a head 38 and a threaded shaft 40 configured for penetrating tissue. It is contemplated that shaft 40 may include engaging structures, such as, for example, a nail configuration, barbs, expanding elements, raised elements and/or spikes to facilitate engagement of shaft 40 with tissue, such as, for example, vertebrae.

Head 38 includes an inner surface that defines a cavity, such as, for example, a U-shaped passageway 42 configured for disposal of tether 28. The inner surface of head 38 is threaded for engagement with a threaded set screw 44. Screw 44 threadably engages head 38 to fix and/or lock tether 28 with bone fastener 36. In one embodiment, an outer surface of head 38 may include a recess or cavity configured to receive an insertion tool, compression instrument and/or instruments for inserting and tensioning bone fastener 36.

A first spacer 46 is disposed adjacent bone fastener 36. Spacer 46 has a rigid configuration and includes an inner surface (not shown) that defines a cavity (not shown). The cavity of spacer 46 is configured for disposal of tether 28 therein. It is envisioned that all or only a portion of spacer 46 may have a semi-rigid, rigid or elastic configuration, and/or have elastic properties such that spacer 46 provides a selective amount of increasing, variable, constant and/or decreasing resistance to movement of vertebrae.

The cavity formed by spacer 46 has a uniform thickness/diameter. It is envisioned that inner surface of spacer 46 may have various surface configurations, such as, for example, rough, threaded for connection with surgical instruments, arcuate, undulating, porous, semi-porous, dimpled, polished and/or textured according to the requirements of a particular application. It is contemplated that the cavity may be uniformly increasing or decreasing, or have alternate diameter dimensions along its length. It is further contemplated that the cavity may have various cross section configurations, such as, for example, oval, oblong, triangular, rectangular, square, polygonal, irregular, uniform, non-uniform, variable and/or tapered.

Spacer 46 includes an inner lateral surface 52 that defines a lateral cavity 54. Surface 52 is threaded for engagement with a threaded set screw 56. Screw 56 threadably engages spacer 46 to fix and/or lock tether 28 with spacer 46.

A second spacer 58 is disposed adjacent to second end 32. Spacer 58 has a rigid configuration and includes an inner surface (not shown) that defines a cavity (not shown). The cavity of spacer 58 is configured for disposal of tether 28 therein. It is envisioned that all or only a portion of spacer 58 may have a semi-rigid, rigid or elastic configuration, and/or have elastic properties such that spacer 58 provides a selective amount of increasing, variable, constant and/or decreasing resistance to movement of vertebrae.

The cavity of spacer 58 has a uniform thickness/diameter. It is envisioned that inner surface of spacer 58 may have various surface configurations, such as, for example, rough, threaded for connection with surgical instruments, arcuate, undulating, porous, semi-porous, dimpled, polished and/or textured according to the requirements of a particular application. It is contemplated that the cavity may be uniformly increasing or decreasing, or have alternate diameter dimensions along its length. It is further contemplated that the cavity may have various cross section configurations, such as, for example, oval, oblong, triangular, rectangular, square, polygonal, irregular, uniform, non-uniform, variable and/or tapered.

Spacer 58 includes an inner lateral surface 64 that defines a lateral cavity 66. Surface 64 is threaded for engagement with a threaded set screw 68. Screw 68 threadably engages spacer 58 to fix and/or lock tether 28 with spacer 58.

A flexible element, such as, for example, a resistance element 70 is disposed about tether 28, and between spacer 46 and spacer 58. Resistance element 70 includes an inner surface 72 that defines a cavity 74. Cavity 74 is configured for disposal of tether 28 therein.

Cavity 74 has a uniform thickness/diameter and defines a central axis c of resistance element 70 that is offset from central axis a of tether 28. Central axis c is disposed within perimeter P of tether 28. This configuration of resistance element 70 with vertebral construct 20 provides a non-concentric intermediate portion 26 for dynamic stabilization applications. It is envisioned that inner surface 72 may have various surface configurations, such as, for example, rough, threaded for connection with surgical instruments, arcuate, undulating, porous, semi-porous, dimpled, polished and/or textured according to the requirements of a particular application. It is contemplated that the cavity 74 may be uniformly increasing or decreasing, or have alternate diameter dimensions along its length. It is further contemplated that cavity 74 may have various cross section configurations, such as, for example, oval, oblong, triangular, rectangular, square, polygonal, irregular, uniform, non-uniform, variable and/or tapered.

Resistance element 70 is flexible and has an arrow shaped cross section that tapers from a broad shaped, arcuate first end 76 to a narrow, pointed second end 78. As such, element 70 provides increased and/or greater resistance adjacent first end 76 and reduced and/or less resistance adjacent second end 78. The adjustment and/or concentration of material regulates the variable resistance of element 70 to movement of sections 22, 24 and 26. This configuration of element 70 provides a selective and/or controlled damping to forces applied to vertebral construct 20.

It is contemplated that element 70 can provide increasing, variable, constant and/or decreasing resistance. Element 70 can be variously configured with regard to size, shape, for example, round, oblong, rectangular, triangular, spherical, and irregular shapes, and can be of monolithic construction. The material of element 70 can be solid or porous, homogeneous or heterogeneous, single polymer or a blend/composite of more than one polymer. It is contemplated that the resiliency of element 70 can prevent creep and improve shape recovery of vertebral construct 20.

A second fixation element, such as, for example, a bone fastener 80 is mounted to tether 28 and disposed between spacer 46 and element 70. Bone fastener 80 is elongated along an axis d, which is oriented transverse to axis a. Bone fastener 80 comprises a head 82 and a threaded shaft 84 configured for penetrating tissue.

Head 82 includes an inner surface that defines a U-shaped passageway 86 configured for disposal of tether 28. The inner surface of head 82 is threaded for engagement with a threaded set screw 88. Screw 88 threadably engages head 82 to fix and/or lock tether 28 with bone fastener 80.

A first cap 90 is disposed adjacent bone fastener 80 and spacer 46. Cap 90 has a rigid configuration and includes an opening (not shown) configured for disposal of tether 28 therein, it is envisioned that all or only a portion of cap 90 may have a semi-rigid, rigid or elastic configuration, and/or have elastic properties such that cap 90 provides a selective amount of increasing, variable, constant and/or decreasing resistance to movement of vertebrae.

Cap 90 defines an outer surface 92, which includes planar sides, configured for engagement with bone fastener 80 and spacer 46. It is envisioned that outer surface 92 may have various surface configurations, such as, for example, rough, threaded for connection with surgical instruments, arcuate, undulating, porous, semi-porous, dimpled, polished and/or textured according to the requirements of a particular application. It is further contemplated that cap 90 may have various configurations, such as, for example, oval, oblong, triangular, rectangular, square, polygonal, irregular, uniform, non-uniform, variable and/or tapered.

A second cap 100 is disposed adjacent hone fastener 80 and flexible element 70. Cap 100 has a rigid configuration and includes an opening (not shown) configured for disposal of tether 28 therein. It is envisioned that all or only a portion of cap 100 may have a semi-rigid, rigid or elastic configuration, and/or have elastic properties such that cap 90 provides a selective amount of increasing, variable, constant and/or decreasing resistance to movement of vertebrae.

Cap 100 defines an outer surface 102, which includes planar sides, configured for engagement with bone fastener 80 and flexible element 70. It is envisioned that outer surface 102 may have various surface configurations, such as, for example, rough, threaded for connection with surgical instruments, arcuate, undulating, porous, semi-porous, dimpled, polished and/or textured according to the requirements of a particular application. It is further contemplated that cap 100 may have various configurations, such as, for example, oval, oblong, triangular, rectangular, square, polygonal, irregular, uniform, non-uniform, variable and/or tapered.

A third fixation element, such as, for example, a bone fastener 110 is mounted to tether 28 and disposed between spacer 58 and resistance element 70. Bone fastener 110 is elongated along an axis e, which is oriented transverse to axis a. Bone fastener 110 comprises a head 118 and a threaded shaft 114 configured for penetrating tissue. It is contemplated that shaft 114 may include engaging structures, such as, for example, a nail configuration, barbs, expanding elements, raised elements and/or spikes to facilitate engagement of shaft 114 with tissue, such as, for example, vertebrae.

Head 118 includes an inner surface that defines a cavity, such as, for example, a U-shaped passageway 112 configured for disposal of tether 28. The inner surface of head 118 is threaded for engagement with a threaded set screw 116. Screw 116 threadably engages head 118 to fix and/or lock tether 28 with bone fastener 110. In one embodiment, an outer surface of head 118 may include a recess or cavity configured to receive an insertion tool, compression instrument and/or instruments for inserting and tensioning bone fastener 118.

A third cap 120 is disposed between bone fastener 110 and flexible element 70. Cap 120 has a rigid configuration and includes an opening (not shown) configured for disposal of tether 28 therein. It is envisioned that all or only a portion of cap 120 may have a semi-rigid, rigid or elastic configuration, and/or have elastic properties such that cap 120 provides a selective amount of increasing, variable, constant and/or decreasing resistance to movement of vertebrae.

Cap 120 defines an outer surface 122, which includes planar sides, configured for engagement with bone fastener 120 and flexible element 70. It is envisioned that outer surface 122 may have various surface configurations, such as, for example, rough, threaded for connection with surgical instruments, arcuate, undulating, porous, semi-porous, dimpled, polished and/or textured according to the requirements of a particular application. It is further contemplated that cap 120 may have various configurations, such as, for example, oval, oblong, triangular, rectangular, square, polygonal, irregular, uniform, non-uniform, variable and/or tapered.

A fourth cap 130 is disposed between bone fastener 110 and spacer 58. Cap 130 has a rigid configuration and includes an opening (not shown) configured for disposal of tether 28 therein, it is envisioned that all or only a portion of cap 130 may have a semi-rigid, rigid or elastic configuration, and/or have elastic properties such that cap 130 provides a selective amount of increasing, variable, constant and/or decreasing resistance to movement of vertebrae.

Cap 130 defines an outer surface 132, which includes planar sides, configured for engagement with bone fastener 110 and spacer 58. It is envisioned that outer surface 132 may have various surface configurations, such as, for example, rough, threaded for connection with surgical instruments, arcuate, undulating, porous, semi-porous, dimpled, polished and/or textured according to the requirements of a particular application. It is further contemplated that cap 130 may have various configurations, such as, for example, oval, oblong, triangular, rectangular, square, polygonal, irregular, uniform, non-uniform, variable and/or tapered.

Figure 3:
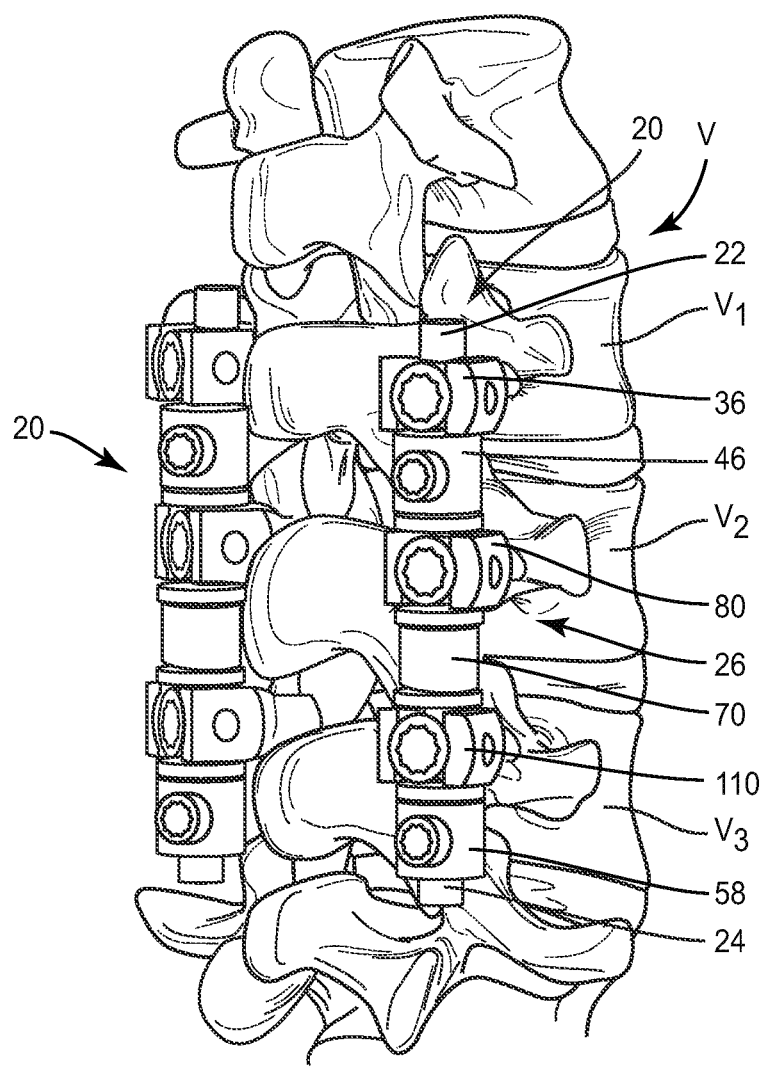
FIG. 3 is a perspective view of the vertebral construct shown in FIG. 1 disposed with vertebrae.
Figure 4:
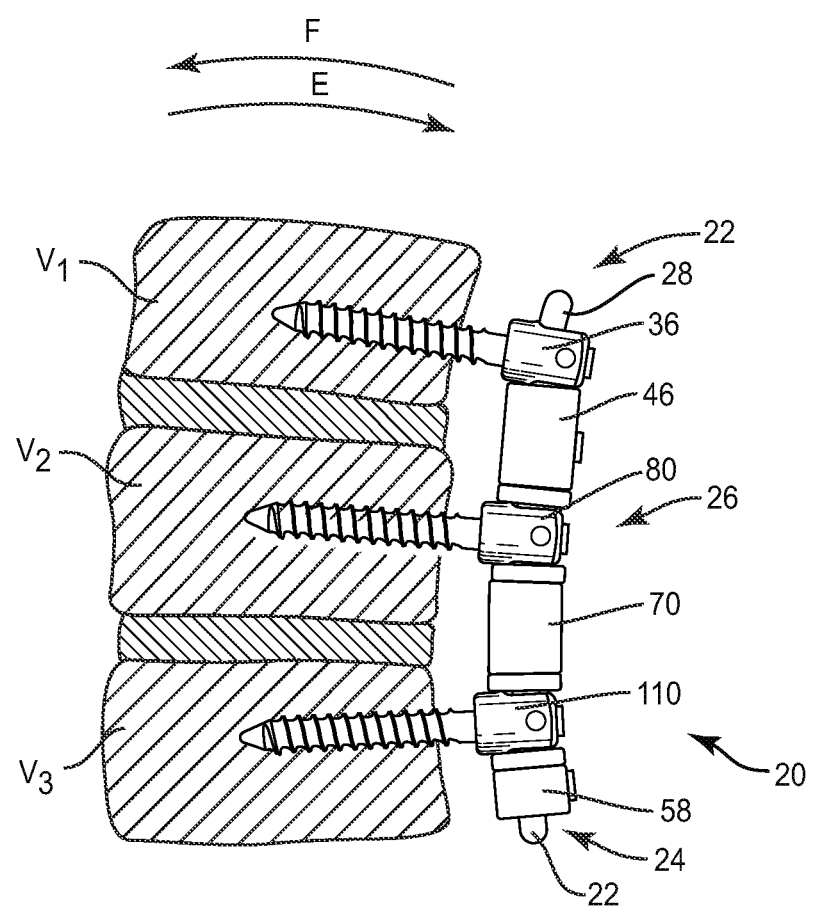
FIG. 4 is a side view, in part cross section, of the vertebral construct and vertebrae shown in FIG. 3.

In assembly, operation and use, vertebral construct 20 is employed with a surgical procedure for treatment of a spinal disorder affecting a section of a spine of a patient, as discussed herein. Vertebral construct 20 may also be employed with other surgical procedures. In particular, vertebral construct 20 is employed with a surgical procedure for treatment of a condition or injury of an affected section of the spine including vertebrae V, as shown in FIGS. 3 and 4. It is contemplated that the vertebral construct is attached to vertebrae V for dynamic stabilization of the affected section of the spine to facilitate healing and therapeutic treatment, while providing flexion and extension capability.

In use, to treat the affected section of the spine, a medical practitioner obtains access to a surgical site including vertebra V in any appropriate manner, such as through incision and retraction of tissues. It is envisioned that vertebral construct 20 may be used in any existing surgical method or technique including open surgery, mini-open surgery, minimally invasive surgery and percutaneous surgical implantation, whereby the vertebrae V is accessed through a micro-incision, or sleeve that provides a protected passageway to the area. Once access to the surgical site is obtained, the particular surgical procedure is performed for treating the spinal disorder. Vertebral construct 20 is then employed to augment the surgical treatment. Vertebral construct 20 can be delivered or implanted as a pre-assembled device or can be assembled in situ.

Bone fastener 36 is configured to attach upper section 22 to vertebra $V_1$. Bone fastener 80 is configured to attach midsection 26 to adjacent vertebra $V_2$. Bone fastener 110 is configured to attach lower section 24 to adjacent vertebra $V_3$. Pilot holes are made in vertebrae $V_1$, $V_2$ and $V_3$ for receiving fixation bone fasteners 36, 80, 110. The shafts of bone fasteners 36, 80, 110 are inserted or otherwise connected to vertebrae $V_1$, $V_2$ and $V_3$ according to the particular requirements of the surgical treatment. The setscrews are torqued onto tether 20 for fixation with bone fasteners 36, 80, 110 in place with vertebrae V.

As shown in FIG. 4, vertebral construct 20 is in an unloaded state, where there is no appreciable tensile or compressive loads on vertebrae $V_1$, $V_2$ and $V_3$. In flexion and/or extension of vertebrae V caused by corresponding movement of the patient, vertebral construct 20 reacts with increasing resistance during movement of vertebral construct 20 to a second, third or more orientation(s).

In flexion, upper section 22 moves relative to section 24, in the direction shown by arrow F. Resistance element 70 flexibly compresses adjacent first end 76. In extension, upper section 22 moves relative to section 24, in the direction shown by arrow E. Resistance element 70 flexibly compresses adjacent second end 78. This configuration provides adjustable resistance and/or variable damping during flexion and extension. As such, element 70 provides increased and/or greater resistance adjacent first end 76 and reduced and/or less resistance adjacent second end 78. The adjustment and/or concentration of material regulates the variable resistance of element 70 to movement of sections 22, 24 and 26. This configuration of element 70 provides a selective and/or controlled damping to forces applied to vertebral construct 20.

Vertebral construct 20 can be used with various bone screws, pedicle screws or multi-axial screws used in spinal surgery. It is contemplated that vertebral construct 20 may be used with pedicle screws coated with an osteoconductive material such as hydroxyapatite and/or osteoinductive agent such as a bone morphogenic protein for enhanced bony fixation to facilitate motion of the treated spinal area.

Figure 5:
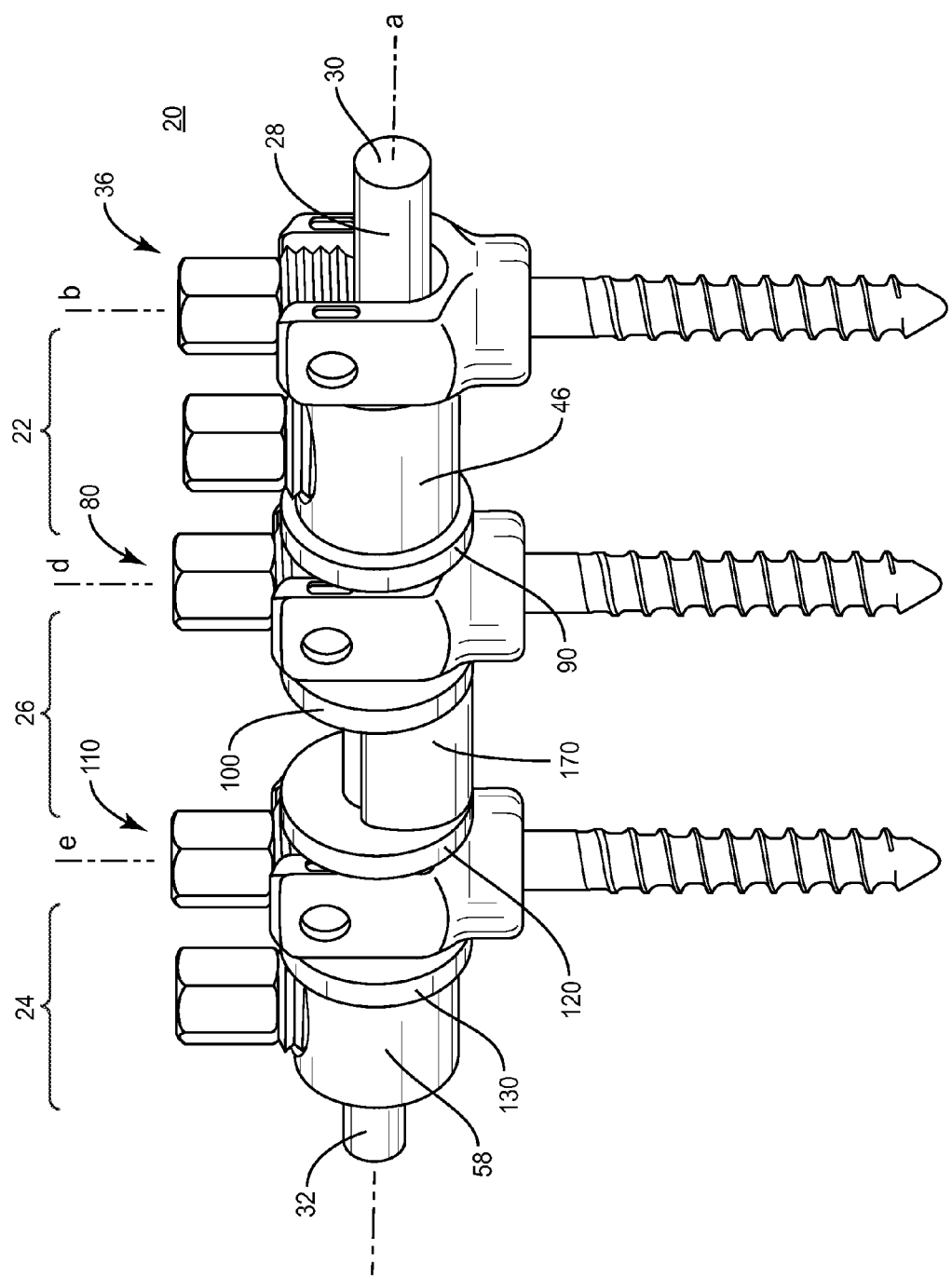
FIG. 5 is a perspective view of one embodiment of the vertebral construct shown in FIG. 1.
Figure 6:
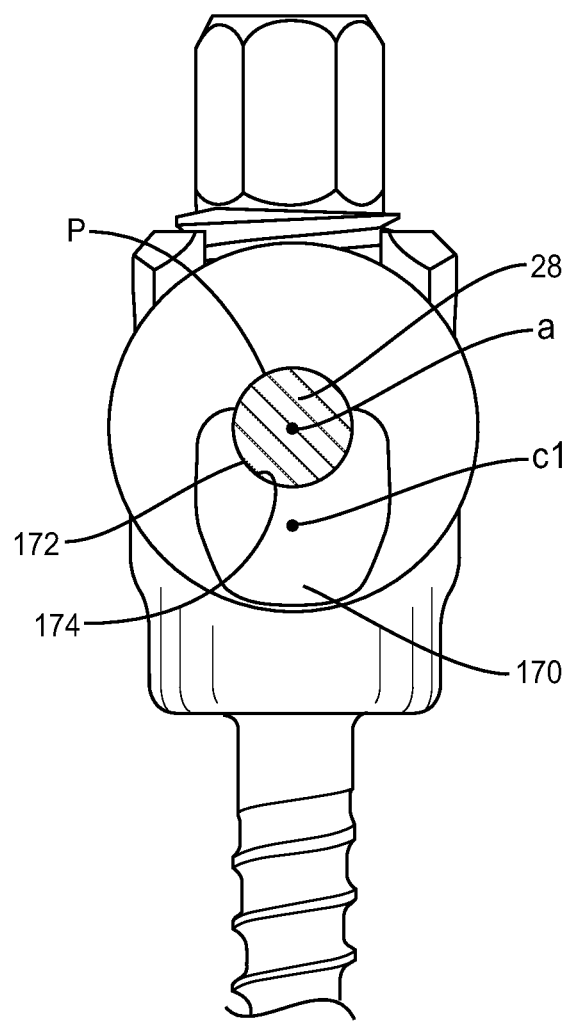
FIG. 6 is a plan view in part cross section of the vertebral construct shown in FIG. 5.

In one embodiment, as shown in FIGS. 5 and 6, vertebral construct 20, similar to that described above with regard to FIGS. 1-4, includes a resistance element 170. Resistance element 170 is disposed about tether 28, and between spacer 46 and spacer 58. Resistance element 170 has a non-uniform C-shaped configuration and includes an arcuate inner surface 172 that defines a hemispherical cavity 174. Cavity 174 is configured for disposal of tether 28 therein.

Cavity 174 has a uniform thickness/diameter and defines a central axis $c_1$ of resistance element 170 that is offset from central axis a of tether 28. Central axis $c_1$ is disposed outside perimeter P of tether 28. This configuration of resistance element 170 with vertebral construct 20 provides a non-concentric intermediate portion 26 for dynamic stabilization applications. Resistance element 170 is flexible and is disposed on anterior side of tether 28. As such, element 170 provides increased and/or greater resistance on anterior side of tether 28 and reduced and/or less resistance on a posterior side of tether 28.

Figure 7:
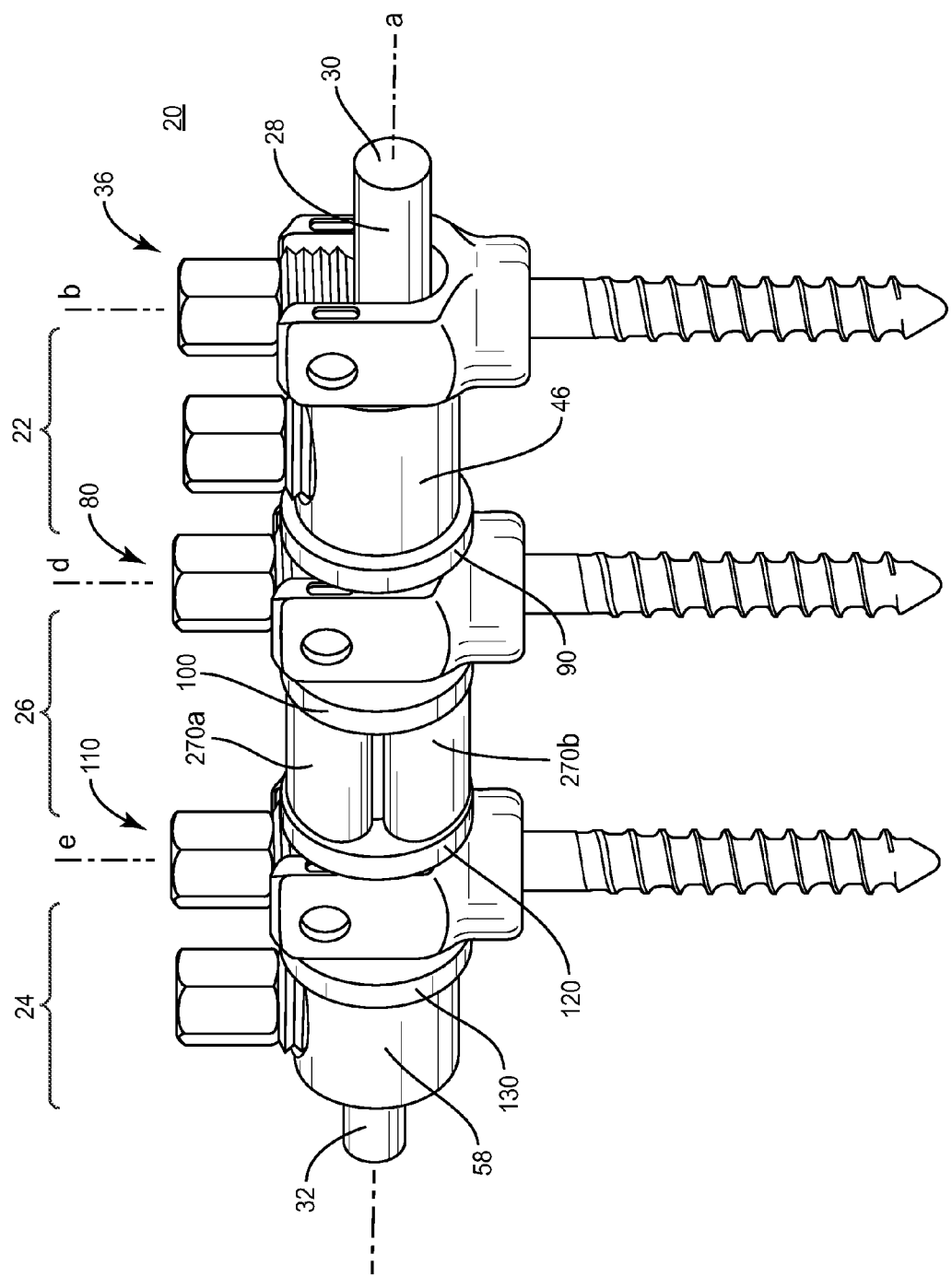
FIG. 7 is a perspective view of one embodiment of the vertebral construct shown in FIG. 1.
Figure 8:
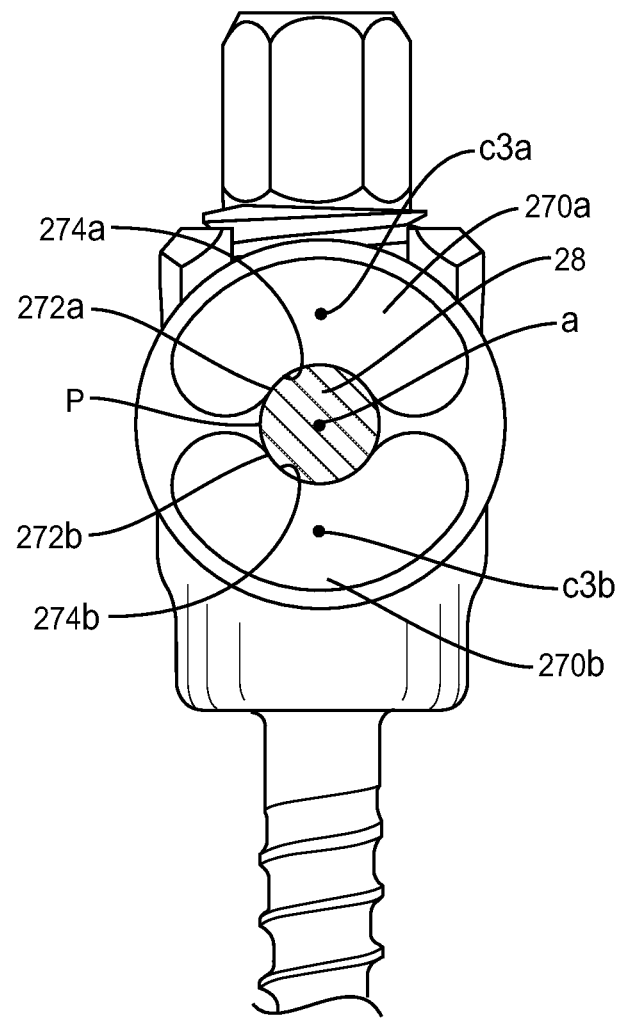
FIG. 8 is a plan view in part cross section of the vertebral construct shown in FIG. 7.

In one embodiment, as shown in FIGS. 7 and 8, vertebral construct 20, similar to that described above with regard to FIGS. 1-4, includes a resistance element 270a and a resistance element 270b. Elements 270a, 270b are disposed about tether 28, and between spacer 46 and spacer 58.

Resistance element 270a includes an arcuate inner surface 272a that defines a hemispherical cavity 274a. Cavity 274a is configured for disposal of tether 28 therein. Cavity 274a has a uniform thickness/diameter and defines a central axis c3a of resistance element 270a that is offset from central axis a of tether 28. Central axis c3a is disposed outside perimeter P of tether 28. This configuration of resistance element 270a with vertebral construct 20 provides a non-concentric intermediate portion 26 for dynamic stabilization applications. Resistance element 270a is flexible and is disposed on a posterior of tether 28. Resistance element 270a has a first resistance.

Resistance element 270b includes an arcuate inner surface 272b that defines a hemispherical cavity 274b. Cavity 274b is configured for disposal of tether 28 therein. Cavity 274b has a uniform thickness/diameter and defines a central axis c3b of resistance element 270b that is offset from central axis a of tether 28. Central axis c3b is disposed outside perimeter P of tether 28. This configuration of resistance element 270b with vertebral construct 20 provides a non-concentric intermediate portion 26 for dynamic stabilization applications. Resistance element 270b is flexible and is disposed on an anterior side of tether 28. Resistance element 270b has a second resistance, which is greater than the first resistance. As such, element 270b provides increased and/or greater resistance on anterior side of tether 28 and element 270a provides reduced and/or less resistance on a posterior side of tether 28.

Figure 9:
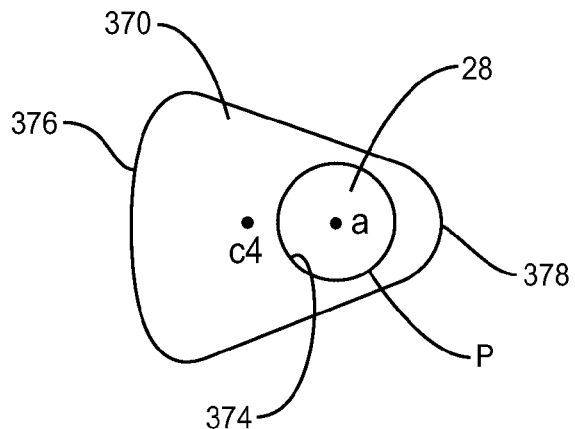
FIG. 9 is a plan view in part cross section of one embodiment of the vertebral construct shown in FIG. 1.

In one embodiment, as shown in FIG. 9, vertebral construct 20, similar to that described above with regard to FIGS. 1-4, includes a resistance element 370. Resistance element 370 is flexible and has an arrow shaped cross section that tapers from a broad shaped, arcuate first end 376 to a narrow, pointed second end 378. Resistance element 370 defines a cavity 374 having a uniform thickness/diameter and defining a central axis c4 of resistance element 370 that is offset from central axis a of tether 28. Central axis c4 is disposed outside perimeter P of tether 28.

Figure 10:
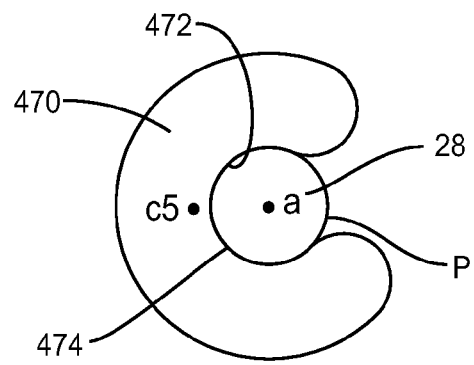
FIG. 10 is a plan view in part cross section of one embodiment of the vertebral construct shown in FIG. 1.

In one embodiment, as shown in FIG. 10, vertebral construct 20, similar to that described above with regard to FIGS. 5 and 6, includes a resistance element 470. Resistance element 470 is disposed about tether 28. Resistance element 470 has a uniform C-shaped configuration and includes an arcuate inner surface 472 that defines a cavity 474. Cavity 474 is configured for disposal of tether 28 therein. Cavity 474 has a uniform thickness/diameter and defines a central axis c5 of resistance element 470 that is offset from central axis a of tether 28. Central axis c5 is disposed outside perimeter P of tether 28. Resistance element 470 is flexible and is disposed on an anterior side of tether 28. As such, element 470 provides increased and/or greater resistance on the anterior side of tether 28 and reduced and/or less resistance on a posterior side of tether 28.

Figure 11:
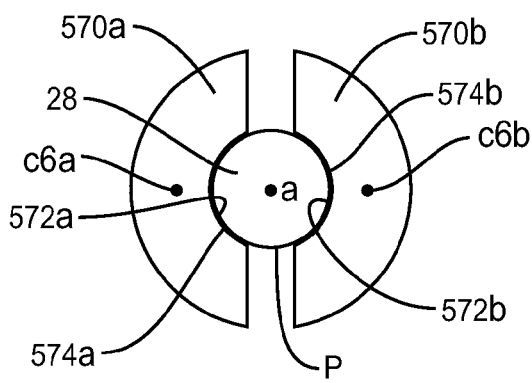
FIG. 11 is a plan view in part cross section of one embodiment of the vertebral construct shown in FIG. 1.

In one embodiment, as shown in FIG. 11, vertebral construct 20, similar to that described above with regard to FIGS. 7 and 8, includes a resistance element 570a and a resistance element 570b. Elements 570a, 570b are disposed about tether 28. Resistance element 570a has a uniform C-shaped configuration and includes an arcuate inner surface 572a that defines a hemispherical cavity 574a. Cavity 574a is configured for disposal of tether 28 therein. Cavity 574a has a uniform thickness/diameter and defines a central axis c6a of resistance element 570a that is offset from central axis a of tether 28. Central axis c6a is disposed outside perimeter P of tether 28. Resistance element 570a is flexible and is disposed on a posterior of tether 28. Resistance element 570a has a first resistance.

Resistance element 570b has a uniform C-shaped configuration and includes an arcuate inner surface 572b that defines a hemispherical cavity 574b. Cavity 574b is configured for disposal of tether 28 therein. Cavity 574b has a uniform thickness/diameter and defines a central axis c6b of resistance element 570b that is offset from central axis a of tether 28. Central axis c6b is disposed outside perimeter P of tether 28. Resistance element 570b is flexible and is disposed on an anterior side of tether 28. Resistance element 570b has a second resistance, which is greater than the first resistance. As such, element 570b provides increased and/or greater resistance on anterior side of tether 28 and element 570a provides reduced and/or less resistance on a posterior side of tether 28.

Figure 12:
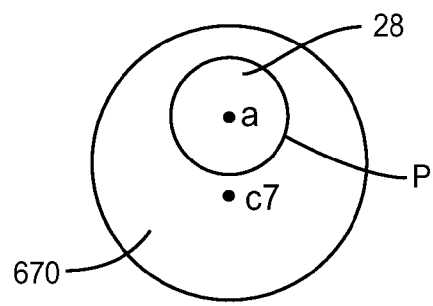
FIG. 12 is a plan view in part cross section of one embodiment of the vertebral construct shown in FIG. 1.

In one embodiment, as shown in FIG. 12, vertebral construct 20, similar to that described above, includes a resistance element 670. Resistance element 670 is disposed circumferentially about tether 28 and surrounds tether 28. Resistance element 670 has a circular configuration and includes an arcuate inner surface 672 that defines a cavity 674. Cavity 674 is configured for disposal of tether 28 therein. Cavity 674 has a uniform thickness/diameter and defines a central axis c7 of resistance element 670 that is offset from central axis a of tether 28. Central axis c7 is disposed outside perimeter P of tether 28.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A vertebral construct comprising:
   a longitudinal element extending between a first end and a second end, and defining a central axis;
   a first spacer mounted to the longitudinal element;
   a second spacer mounted to the longitudinal element;
   a flexible element disposed about the longitudinal element and between the first spacer and the second spacer, the flexible element defining a central axis offset from the central axis of the longitudinal element;
   a first bone fastener mounted to the longitudinal element and being disposed between the first spacer and the flexible element; and
   a first cap being disposed between the first bone fastener and the first spacer and configured for disposal of the longitudinal element.

2. The vertebral construct of claim 1 wherein the longitudinal element includes a flexible tether.

3. The vertebral construct of claim 1 wherein the first spacer as a rigid configuration.

4. The vertebral construct of claim 1, wherein each of the first spacer and the second space a have a rigid configuration.

5. The vertebral construct of claim 1, further comprising a second bone fastener mounted to the longitudinal element and being disposed between the second spacer and the flexible element.

6. The vertebral construct of claim 1, wherein the first cap is rigid, and further comprising a second rigid cap being disposed between the first bone fastener and the flexible element.

7. The vertebral construct of claim 6, further comprising a second bone fastener mounted to the longitudinal element and being disposed between the second spacer and the flexible element, a third rigid cap being disposed between the first bone fastener and the first spacer, and a fourth rigid cap being disposed between the first bone fastener and the flexible element.

8. The vertebral construct of claim 1, wherein the longitudinal element defines a perimeter and the central axis of the flexible element is disposed within the perimeter.

9. The vertebral construct of claim 1, wherein the longitudinal element defines a perimeter and the central axis of the flexible element is disposed outside the perimeter.

10. The vertebral construct of claim 1, wherein the flexible element is tapered from a first end to a second end thereof.

11. The vertebral construct of claim 1, wherein the flexible element is selectively disposed about the longitudinal element to provide a variable resistance during movement.

12. The vertebral construct of claim 1, wherein the flexible element includes a first flexible member having a first resistance and a second flexible member having a second resistance.

13. The vertebral construct of claim 12, wherein the first resistance is greater than the second resistance.

14. The vertebral construct of claim 1, wherein the flexible element extends from a first end to a second end such that the first end has a first resistance and the second end has a second resistance to provide a selective damping across the flexible element during movement.

15. The vertebral construct of claim 1, wherein the first bone fastener defines a longitudinal axis extending transverse to the central axis of the longitudinal element that does not intersect the first spacer, the second spacer or the flexible member.

16. A vertebral construct comprising:
a longitudinal element extending between a first end and a second end, and defining a central axis;
a first rigid spacer including an inner surface that defines a cavity configured for disposal of the longitudinal element therein;
a second rigid spacer including an inner surface that defines a cavity configured for disposal of the longitudinal element therein;
a resistance element including an inner surface that defines a cavity configured for disposal about the longitudinal element, the resistance element being further disposed between the first spacer and the second spacer, the resistance element defining a central axis offset from the central axis of the longitudinal element;
a first bone fastener mounted to the longitudinal element and being disposed between the first spacer and the flexible element; and
a first cap being disposed between the first bone fastener and the first spacer and configured for disposal of the longitudinal element.

17. The vertebral construct of claim 16, wherein the resistance element is selectively disposed about the longitudinal element to provide a variable resistance during movement.

18. The vertebral construct of claim 16, wherein the resistance element includes a first flexible member having a first resistance and a second flexible member having a second resistance, the first resistance being greater than the second resistance.

19. The vertebral construct of claim 16, wherein the resistance element extends from a first end to a second end such that the first end has a first resistance and the second end has a second resistance to provide a selective damping across the resistance element during movement.

20. A vertebral construct comprising:
a tether extending between a first end and a second end, and defining a central axis;
a first fixation element mounted adjacent the first end of the tether;
a first rigid spacer including an inner surface that defines a cavity configured for disposal of the tether therein, the first rigid spacer being disposed adjacent the first fixation element;
a second rigid spacer including an inner surface that defines a cavity configured for disposal of the tether therein;
a resistance element including an inner surface that defines a cavity configured for disposal about the tether, the resistance element being further disposed between the first spacer and the second spacer, the resistance element defining a central axis offset from the central axis of the tether;
a second bone fastener mounted to the tether and being disposed between the first spacer and the resistance element;
a first rigid cap being disposed between the second bone fastener and the first spacer;
a second rigid cap being disposed between the second bone fastener and the resistance element;
a third bone fastener mounted to the tether and being disposed between the second spacer and the resistance element;
a third rigid cap being disposed between the third bone fastener and the resistance element; and
a fourth rigid cap being disposed between the third bone fastener and the second spacer.

* * * * *